United States Patent [19]
Akay et al.

[11] Patent Number: 5,638,823
[45] Date of Patent: Jun. 17, 1997

[54] SYSTEM AND METHOD FOR NONINVASIVE DETECTION OF ARTERIAL STENOSIS

[75] Inventors: Metin Akay, East Brunswick; Walter Welkowitz, Metuchan; Yasemin M. Akay, East Brunswick; John Kostis, Warren, all of N.J.

[73] Assignee: Rutgers University, Piscataway, N.J.

[21] Appl. No.: 520,236

[22] Filed: Aug. 28, 1995

[51] Int. Cl.$^6$ ........................................ A61B 5/00
[52] U.S. Cl. .................. 128/691; 128/668; 128/687; 128/713
[58] Field of Search ................ 128/668, 670, 128/691, 687, 710, 713, 715, 690

[56] References Cited

U.S. PATENT DOCUMENTS

| | | | |
|---|---|---|---|
| 4,967,760 | 11/1990 | Bennett, Jr. et al. | 128/715 |
| 5,036,857 | 8/1991 | Semmlow et al. | 128/715 |
| 5,218,969 | 6/1993 | Biedesen et al. | 128/710 |
| 5,276,612 | 1/1994 | Selker | 128/668 |

OTHER PUBLICATIONS

M. Akay et al., "Acoustical Detection of Coronary Occlusions Using Neural Networks", Nov. 1993, J. Biomed. Eng., pp. 469–473.

M. Akay et al., "Investigating the Effects of Vasodilator Drugs on the Turbulent Sound Caused by Femoral Artery Stenosis Using Short–Term Fourier and Wavelet Transform Methods", Oct. 1994, IEEE Transactions, vol. 41, pp. 921–928.

M. Akay, "Noninvasive Diagnosis of Coronary Artery Disease Using a Neural Network Algorithm", (1992), Biological Cybernetics, pp. 361–367.

S. Mallat et al., "Characterization of Signals from Multiscale Edges", Jul. 1992, IEEE Transactionson Pattern Analysis and Machine Intelligence, vol. 14, pp. 710–732.

*Primary Examiner*—Robert L. Nasser
*Attorney, Agent, or Firm*—Edward S. Irons

[57] ABSTRACT

A system and method for noninvasively detecting coronary artery disease. The system and method utilize a vasodilator drug to increase the signal-to-noise ratio of an acoustic signal that represents diastolic heart sounds of a patient. A wavelet transform is performed on the acoustic signal to provide parameters for a feature vector. Scaled clinical examination parameters such as a patient's sex, age, body weight, smoking condition, blood pressure, and family history are also included in the feature vector. The feature vector is used as an input pattern to neural networks. The output of the neural networks represent a diagnosis of coronary stenosis in a patient.

13 Claims, 6 Drawing Sheets

Time, msec

SYSTEM AND METHOD FOR NONINVASIVE DETECTION OF ARTERIAL STENOSIS

BACKGROUND OF THE INVENTION

1. Field of the Invention

The invention relates generally to the field of acoustical signal processing, more particularly to the detection of arterial stenosis using wavelet transforms and neural networks.

2. Description of Background Art

Coronary artery disease (CAD) is one of the leading causes of death in the world with approximately one third of all deaths attributed to this disease. Accordingly, early detection of coronary artery disease is an important medical research goal.

Several methods exist for the diagnosis of coronary artery disease. These methods can be classified generally as being either noninvasive or invasive. Noninvasive diagnosis methods do not involve penetration of the skin or entry into the body through any natural openings. Noninvasive diagnosis methods include: the physical exam and history method; electro-cardiogram (ECG) techniques such as exercise testing, vectorcardiograms, and apex cardiogram; ultrasound examination, e.g., echocardiography; and imaging examination, e.g., roentgenograms, tomography, and nuclear magnetic resonance. The problem with current noninvasive diagnosis methods is that they have only a moderately successful accuracy rate for diagnosing coronary artery disease.

Invasive diagnosis methods are frequently more reliable than noninvasive diagnosis methods. One of the most reliable technique for diagnosing CAD is cardiac catherization (cath.). In this technique a catheter is inserted into an artery, e.g., a brachial or femoral artery, and advanced to the heart. Once in the heart, dye can be released to observe the coronary arteries. Although direct assessment of a coronary occlusion is conclusive, this technique is expensive, painful, time consuming, and has a significant risk to the patient, e.g., the mortality rates can range from 0.2%–7%.

Another invasive diagnosis method is referred to as the thallium test. In the thallium test, thallium-201, a radiopharmaceutical substance with biological properties similar to potassium and commercially available, is used to detect myocardial ischemia in patients with CAD. When given invasively, its myocardial distribution is proportional to myocardial blood flow. Therefore, low blood flow regions accumulate less thallium and appear as cold spots on the image obtained from a camera that is located over the precordium. Although the sensitivity of the thallium test is 83%, and its specificity is 90%; it is costly and time consuming to implement.

What is needed is a reliable, inexpensive, noninvasive diagnosis technique that will enable coronary artery disease to be detected at an early stage of development.

SUMMARY OF THE INVENTION

The invention is a system and method for noninvasively detecting coronary artery disease. The system and method utilize a vasodilator drug to increase the signal-to-noise ratio of an acoustic signal that represents diastolic heart sounds of a patient. A wavelet transform is performed on the acoustic signal to provide parameters for a feature vector. Scaled clinical examination parameters such as a patient's sex, age, body weight, smoking condition, blood pressure, and family history are also included in the feature vector. The feature vector is used as an input pattern to neural networks. The output of the neural networks represent a diagnosis of coronary stenosis in a patient.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit of each reference number corresponds to the figure in which the reference number is first used.

The invention is directed to a system and method for detecting arterial stenosis having a number of features, including (1) using a drug, e.g., a vasodilator drug, to increase the signal-to-noise ratio of the acoustic signal from the artery, (2) performing a wavelet transform on the acoustic signal to filter the acoustic signal, (3) generating a feature vector having parameters from an output signal of the wavelet transform and parameters from a clinical examination of the patient, and (4) sending the feature vector to a fuzzy min-max neural network to diagnose whether the patient has arterial stenosis.

One embodiment of the present invention detects coronary stenosis. It is known that coronary stenosis generates an auditory component, e.g., a murmur, due to turbulent blood flow in partially occluded coronary arteries. Typically this auditory component is not present in a healthy patient. However, efforts to detect this auditory component have met with limited success. One reason for this is that the auditory component associated with coronary stenosis is weak and heavily contaminated with noise. In addition, its detection—by way of an acoustic transducer—is heavily attenuated due to the intervening heart tissue, the chest wall, and other tissues, such as lung or fat tissues. Detection is also difficult because of the comparatively loud heart valve sounds as well as other naturally occurring body sounds and external ambient noise.

Studies involving turbulent blood flow have been carried out in many areas of the cardiovascular system and it has been widely reported that turbulence produced by stenoses produce sounds due to the vibration of the surrounding structures, see, M. Akay et al., *Detection of Coronary Occlusions Using AR Modeling of Diastolic Heart Sounds*, IEEE Trans. on Biomed. Eng., 37:366–373, (1990), that is herein incorporated by reference in its entirety. These sounds have been detected and analyzed, and results generally show that the high frequency energy of the acoustic signal increased when the degree of stenosis was increased. The auditory component associated with coronary stenosis is similar to that found in partially occluded carotid arteries, but is more attenuated because of the greater depth of intervening tissue. It is also masked by the comparatively loud valve sounds. The affect of these valve sounds can be reduced by isolating the diastolic portions of the acoustic signal and by analyzing signals during a time period that is synchronized with the diastolic period of the cardiac cycle. In addition to reducing the affect of the valve noise, it is during diastole that coronary blood flow is at a maximum and the sounds associated with turbulent blood flow through partially occluded coronary arteries are the loudest.

Figure 1:
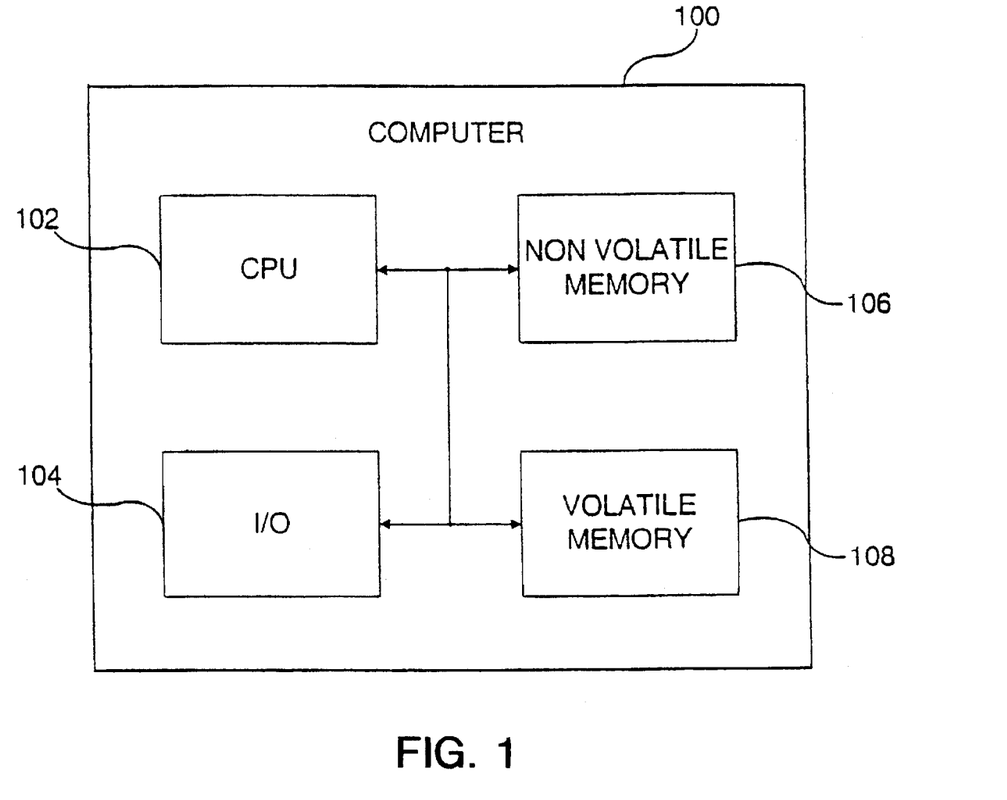
FIG. 1 is an illustration of a computer system in which acoustic signals are analyzed according to the preferred embodiment of the present invention.

FIG. 1 is a block diagram of a computer system 100 in which acoustic signals are analyzed according to the preferred embodiment of the present invention. Examples of the computer system 100 include a personal computer, e.g., an IBM computer (or compatible), available from IBM Corp., Armonk, N.Y., or a Macintosh Computer, commercially available from Apple Computer, Inc., Cupertino, Calif., and a workstation, e.g., a SPARC Station 10 from Sun Microcomputers, Inc., Mountain View, Calif. The computer system 100 includes a central processing unit (CPU) 102, e.g., an Intel Pentium processor, commercially available from Intel Corp., Santa Clara, Calif. The CPU 102 is coupled to a conventional input-output controller I/O 104. The CPU 102 is also coupled to both non-volatile memory 106, e.g., a conventional hard disk storage area or a floppy disk, and a volatile memory 108, e.g., conventional random access memory (RAM). During computer operation, the contents of the non-volatile memory 106 are typically transferred to the volatile memory 108 in order to be executed by the CPU 102. The contents of the non-volatile memory 106 are discussed in greater detail below with reference to FIG. 2.

Figure 2:
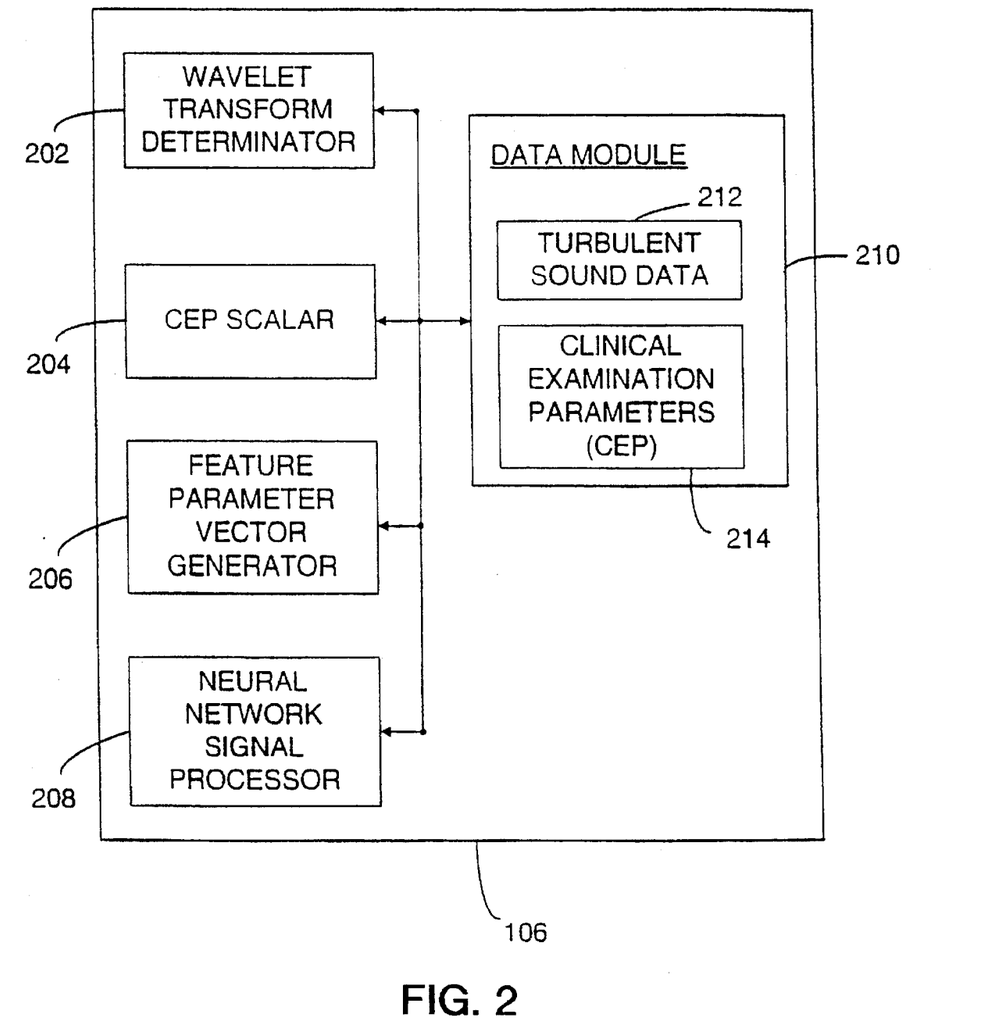
FIG. 2 is a more detailed illustration of the non-volatile memory module of the preferred embodiment.

FIG. 2 is a more detailed illustration of the non-volatile memory module 106 of the preferred embodiment. A data module 210 includes turbulent sound data 212 and clinical examination parameter data (CEP). Techniques for obtaining this data is set forth below with reference to FIG. 3. The data module 210 is coupled to a wavelet transform determinator 202, a CEP scaler 204, a feature parameter vector generator 206, and a neural network signal processor 208. The functions performed by these elements is described in detail below with reference to FIGS. 3–6.

Figure 3:
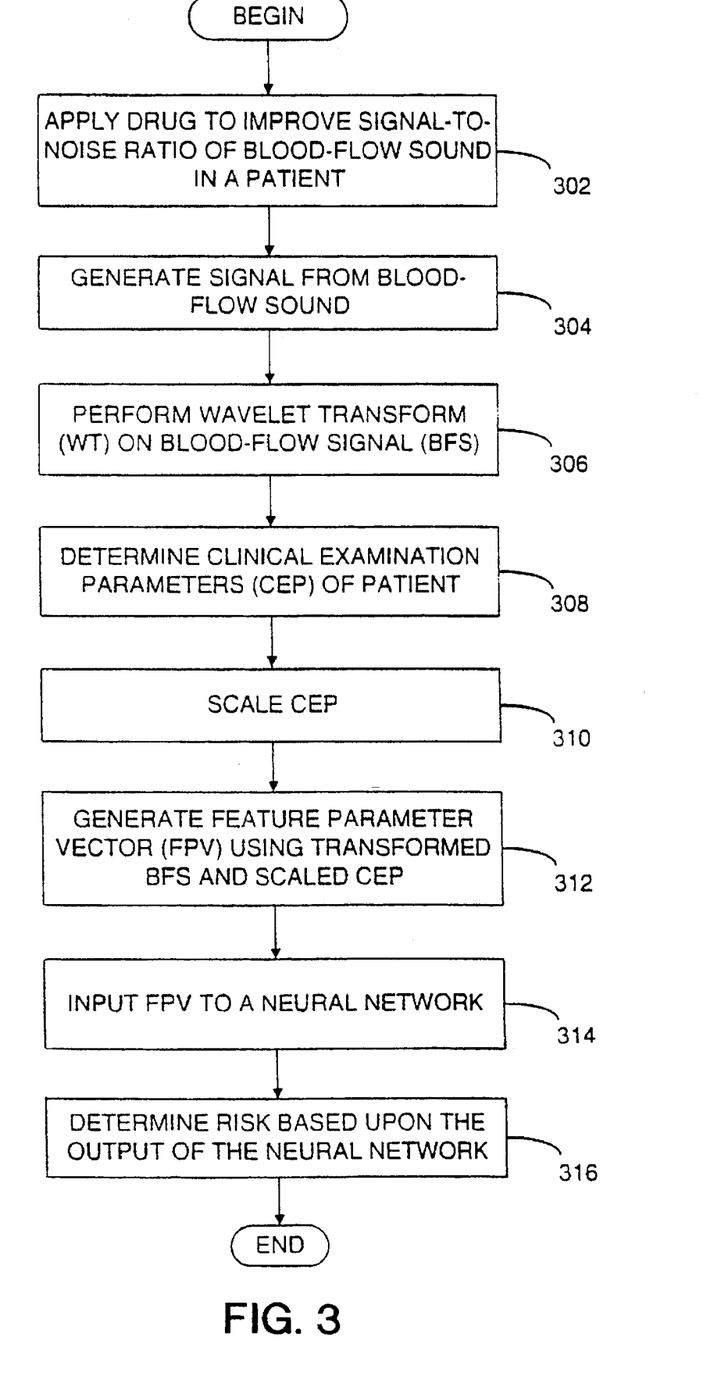
FIG. 3 is a flow chart describing the method of the preferred embodiment of the present invention.

FIG. 3 is a flow chart describing the method of the preferred embodiment of the present invention. As discussed above, one of the difficulties in detecting and analyzing the acoustic signals from occluded coronary arteries are that these signals, when measured on the chest of the patient, have a low signal-to-noise ratio. A technique for increasing the signal-to-noise ratio of the acoustic signals received at the chest is to apply 302 a vasodilator drug, e.g., Papaverine, that is commercially available from Merck, Inc., located in New Jersey. Papaverine is a potent, fast response vasodilator that has an immediate effect on the distal arterioles and capillary bed. Papaverine relaxes the smooth musculature of the large blood vessels, especially the coronary, systemic peripheral, and pulmonary arteries. It also increases cerebral vascular resistance in normal subjects and does not change the oxygen consumption of the patient. More details concerning the effect of vasodilator drugs and the experimental setup are described in M. Akay, et al., *Investigating the Effects of Vasodilator Drugs on the Turbulent Sound Caused by Femoral Artery Stenosis Using Short-Term Fourier and Wavelet Transform Methods*, IEEE Trans. on Biomed. Eng. 41:921–927 (October 1994), and Y. M. Akay, et al., *Dynamics of the Turbulent Sounds Caused by Partially Occluded Femoral Arteries in Dogs*, Proc. IEEE 18th Ann. NE Conf. Biomed. Eng., RI (1992), that are both hereby incorporated by reference in their entirety.

The present invention measures the heart sound after the vasodilator drug increases the blood flow and, hence, the signal-to-noise ratio of the acoustic signal representing the blood flow turbulence caused by an occlusion. The audible sounds from the heart are preferably measured in a soundproof room, to minimize transient noise, using conventional acoustic equipment such as a conventional microphone, available from Hewlett Packard, Palo Alto, Calif., or a commercially available accelerometer transducer. As discussed above, the acoustic measurements are taken during diastole. In the present invention a timing reference indicative of a particular point in the cardiac cycle is used in analyzing the detected heart sounds. An electro-optical pulse detector may be mounted to a finger of the patient. The electro-optical pulse detector and an associated amplifier provide an output signal based upon the occurrence of each pulse of the patient. This output signal provides a timing reference for the cardiac cycle. Alternatively, other techniques can be used to provide a timing reference for the cardiac cycle, for example, a conventional electro-cardiogram (ECG) signal that is processed by a conventional QRS detector. The resulting blood-flow signal (BFS) is stored in the turbulent sound data module 212. A more detailed discussion is given in U.S. Pat. No. 5,036,857 to Semmlow et al., that is hereby incorporated by reference in its entirety.

After the BFS is generated, the wavelet transform determinator 202 analyzes the BFS using a wavelet transform. Wavelet transforms are an important new tool in signal analysis. The characterization of a signal using a wavelet transform provides information on both frequency and temporal localization of the events, e.g., occlusions, in the acoustic signal. In contrast, previous systems use the fourier transform. After a time window has been chosen for the fourier transform, the time-frequency resolution will be fixed over the entire data. Accordingly, the fourier transform provides either good time resolution or good frequency resolution, but not both. Most useful information contained in a BFS is a result of irregular structures, e.g., occlusions, and transient phenomena. As discussed above, in previous systems signals have been analyzed using the fourier transform. The Fourier transform is global and provides a description of the overall regularity of signals. However, in addition to the drawbacks described above, it may not be appropriate for finding the location and the spatial distribution of singularities, e.g., acoustic irregularities from arterial occlusions. The local maxima of a wavelet transform modulus represent the locations of irregular structures represented by the acoustic signal. The preferred embodiment of the present invention utilizes the fast wavelet transform disclosed in S. G. Mallat, S. Zhong, *Characterization of Signals from Multiscale Edges*, IEEE Transactions on PAMI, 10:710–732 (1992), that is hereby incorporated by reference in its entirety.

The integral of a smoothing function, $\phi(t)$, is equal to 1 and converges to 0 at infinity. The smoothing function is gaussian and is differentiable, where $\psi(t)$ is the first-order derivative of $\phi(t)$, as shown in equation (1).

$$\psi(t) = \frac{\partial \phi(t)}{\partial t} \quad (1)$$

The function ψ(t), is a wavelet function because its integral is equal to zero as shown in equation (2).

$$\int_{-\infty}^{\infty} \psi(t)\partial t = 0 \quad (2)$$

The wavelet transform of f(t) at the scale s and position t, computed with respect to the wavelet ψ(t), is defined in equation (3).

$$W_s f(t) = f * \psi_s(t) \quad (3)$$

The wavelet transform $W_s f(t)$, is the first derivative of the signal smoothed at the scale s.

To allow fast numerical implementations, the scale was varied along the dyadic sequence $2^j$. The dilation of $\psi 2^j$ by a factor of $2^j$ is set forth in equation (4).

$$\psi_{2^j}(t) = \frac{1}{2^j} \psi \frac{t}{2^j} \quad (4)$$

The wavelet transform of f(t) at the scale $2^j$ and at the position t is defined by the convolution product as set forth in equation (5).

$$W_{2^j} f(t) = f * \psi_{2^j}(t) \quad (5)$$

The wavelet function, e $\psi 2^j(t)$ is characterized by discrete filters H and G. The discrete filters $H_p$, $G_p$ can be obtained by putting $2^P - 1$ zeros between each of the coefficients of the filters H and G. The transfer function of these filters is $H(2^P w)$ and $G(2^P w)$.

The discrete wavelet transform of the discrete signal:

$$A_1^d f$$

can be estimated using the fast wavelet transform disclosed in the Mallat reference discussed above.

At each scale $2^j$, the fast wavelet transform decomposes $A_{2^j}^d f$ into $A_{2^{j+1}}^d f$ and $W_{2^{j+1}}^d f$ as shown below:

j = 0 while(j < J)

$$W_{2^{j+1}}^d f = \frac{1}{\lambda_j} A_{2^j}^d f * G_j$$

$$A_{2^{j+1}}^d f = A_{2^j}^d f * H_j$$

End while

The constants, $\lambda_j$, compensate for the discretization errors. A more detailed discussion of the wavelet transform is disclosed in the Mallet reference that was previously incorporated herein.

Previous systems and methods for diagnosing coronary artery disease do not automatically combine clinical data with acoustic signals. In the present invention a clinical examination is performed and various parameters are determined 308 and are stored in the clinical examination parameters (CEP) module 214. The determination 308 of the CEP can be done before or concurrent with steps 302–306. The CEP can include the age, sex, body weight, smoking condition, systolic blood pressure, diastolic blood pressure, family history, and blood PH of the patient, to name a few. The CEP's are scaled 310 by the CEP scaler 204 to permit an easier and more accurate signal manipulation when combined with the transposed BFS. A variety of techniques can be used to scale the CEP.

In the preferred embodiment the CEP's are scaled to a value between zero and one, inclusive, where a value of 1.0 represents the highest risk of heart disease for each category. For example, since men are more likely to develop coronary heart stenosis than women, the sex parameter for male patients is scaled to 1.0 while the sex parameter for female patients are scaled to 0.0. The age parameter is scaled to: 0.0 for patients who are less than thirty years of age, 1.0 for patients older than 60 years of age, and for patients between the ages of 30 and 60 the age parameter is interpolated between 0.0 and 1.0. Similarly, the weight parameter of the patient is: 0.0 if the patient is approximately 30 pounds underweight for the patient's age and sex, 1.0 if the patient is approximately 30 pounds overweight, and interpolated for patients whose weight is between 30 pounds underweight and 30 pounds overweight. If the patient smokes, the smoking parameter is scaled to 1.0, otherwise it is scaled to 0.0. The systolic blood pressure parameter is scaled to: 1.0 if the patient's systolic blood pressure exceeds 150, 0.0 if the patient's systolic blood pressure is lower than 120, and between 0.0 and 1.0 if the patient's systolic blood pressure is between 120 and 150. Likewise, the diastolic blood pressure is scaled to: 1.0 if the patient's diastolic blood pressure exceeds 100, 0.0 if the patient's diastolic blood pressure is lower than 80, and between 0.0 and 1.0 if the patient's diastolic blood pressure is between 80 and 100. Many other parameters, e.g., cholesterol level and blood PH level, can also be determined and scaled in a similar manner.

After performing 306 the wavelet transform on the BFS and scaling 310 the CEPs, the feature parameter vector generator 206 generates 312 a feature parameter vector (FPV). The FPV contains parameters associated with the each of the CEPs, as described above, and with the transformed BFS. Although a variety of characterizations of the transformed BFS can be used as inputs to the FPV, the preferred embodiment uses the first four moments of the (wavelet) transformed BFS. The four moments of the transformed BFS are now described.

When a set of values has a sufficiently strong central tendency, that is, a tendency to cluster around some particular value, it is useful to characterize the set by a few numbers that are related to its moments, i.e., the sums of integer powers of the values. A first moment is the mean (or median or mode) of the values which estimates the value around which central clustering occurs. A second moment characterizes the width or variability around the first moment. A common measure of the second moment is the variance or standard deviation of the transformed BFS. A third moment characterizes the degree of asymmetry of a distribution around its mean. One measure of the third moment is the "skewness" of the transformed BFS. While the mean, variance, and standard deviation are dimensional quantities, that is, they have the same units as the measured quantities, the skewness is conventionally defined in such a way as to make in nondimensional. It is a representation of the shape of the distribution. A fourth moment characterizes the peakedness or flatness of a distribution relative to a normal distribution. One measure of the fourth moment is the "kurtosis" of the transformed BFS. The kurtosis is also a nondimensional quantity. A distribution with positive kurtosis is termed "leptokurtic", e.g., the outline of the Matterhorn. A distribution with negative kurtosis is termed platykurtic. These conventional four moments are utilized by the present invention to characterize the transformed BFS and are part of the FPV.

After generating the FPV, it is input 314 into the neural network signal processor 108. Artificial neural networks are a powerful tool in analyzing signals. The application of artificial neural networks (ANNs) has opened a new area for solving problems that are difficult to solve using other signal processing techniques. A multi-layer perceptron can be trained by adjusting the connection weights and changing the unit threshold values. These networks have been widely trained using a backpropagation algorithm which is useful in training these networks. The present invention uses a combination of neural networks and fuzzy systems by using neural network nodes as fuzzy sets and using fuzzy set operations during learning to replace the crisp decision boundaries of the perceptron neural network with the fuzzy hyperplane decision boundaries of the fuzzy neural networks. A detailed discussion of the fuzzy neural network is given in Simpson, *Fuzzy Min-Max Neural Networks-Part 1: Classification*, IEEE Trans. on Neural Networks, 3:776–786 (September, 1992), that is hereby incorporated by reference in its entirety. Although many fuzzy neural networks can be used, the preferred embodiment uses the fuzzy min-max neural network models proposed in the above referenced article by Simpson. Alternatively a probabilistic neural network can also be used.

Figure 4:
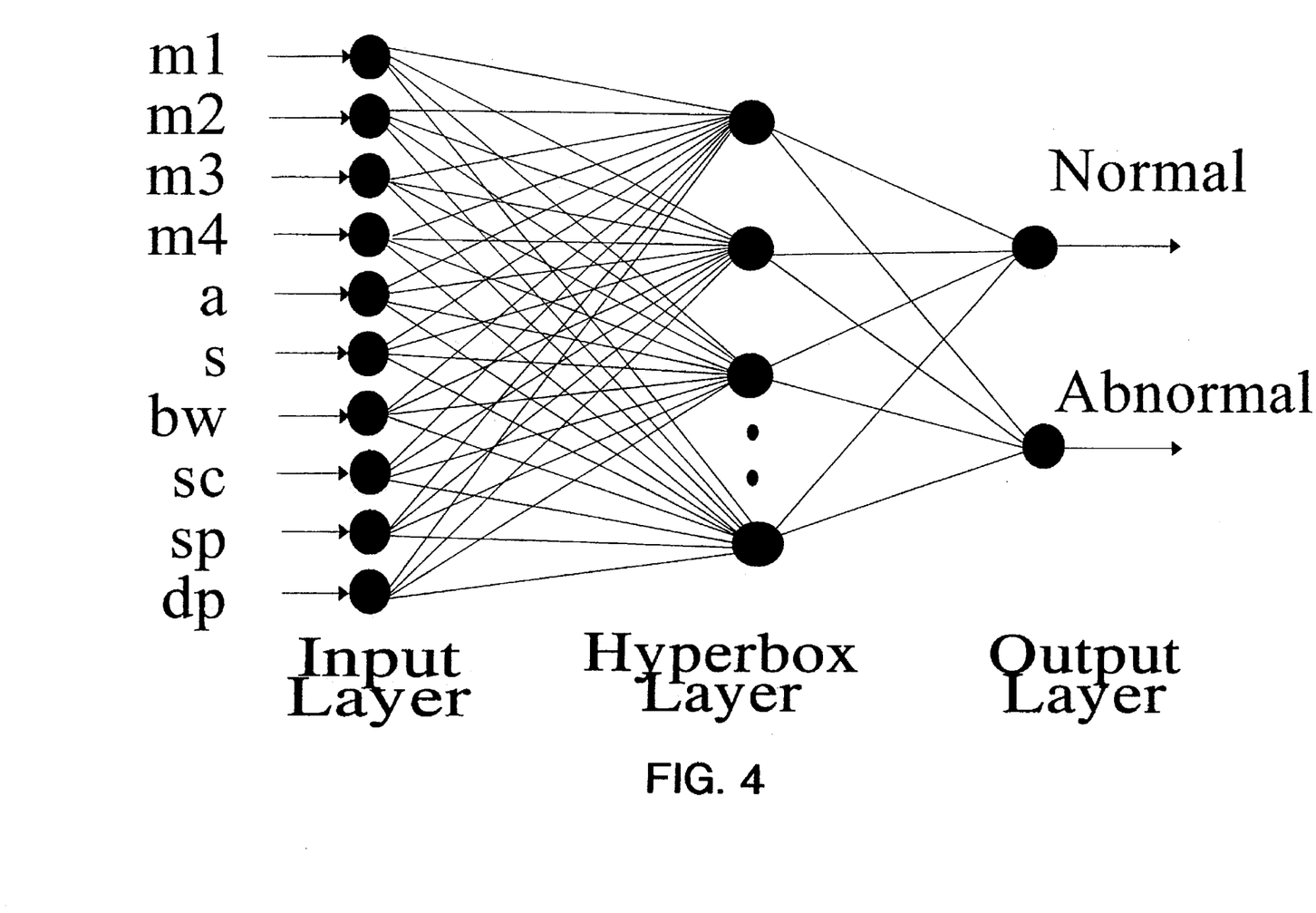
FIG. 4 is an illustration of a three-layer neural network that implements a fuzzy min-max neural network according to the preferred embodiment of the present invention.

Fuzzy min-max neural networks are constructed using hyperbox fuzzy sets. A hyperbox determines a region of n-dimensional pattern space that has patterns with full class membership. Each hyperbox is defined by its minimum and maximum points. A hyperbox membership function is determined by these min-max points. The combination of these hyperbox membership functions constitutes a fuzzy set. Learning in the fuzzy min-max neural network can be done by placing and adjusting hyperboxes in the pattern space. FIG. 4 illustrates a three-layer neural network that implements a fuzzy min-max neural network. The input layer has n processing elements. The input nodes are connected to the second layer consisting of the m hyperbox fuzzy set nodes by two sets of connections—the minimum point vectors and the maximum point vectors. The connections between the hyperbox and the output layers are binary and each node in the output layer represents a pattern class. Fuzzy min-max learning is a series of extension and contraction processes. Learning is accomplished by finding a hyperbox for the same class that can expand (if necessary) to include the input. If a hyperbox that satisfies the expansion criteria is not included, a new hyperbox is included and added to the neural network. As described in the Simpson reference incorporated above, the fuzzy min-max classification learning algorithm can be summarized as:

1. Expansion: determine the hyperbox that can be expanded and expand it. Otherwise, add a new hyperbox for that class.

2. Item Contraction: determine if any overlap exists between hyperboxes from different classes. If any overlap exists between hyperboxes that represent different classes, eliminate the overlap by minimally adjusting the hyperboxes.

As stated above, a more detailed description of the fuzzy min-max neural networks is found in the Simpson reference.

An experiment using the heart sound recordings from 112 patients was performed. The results are now discussed. Diastolic heart sounds were recorded in a soundproof room at the patient's bedside. Patients were selected from those undergoing catherization and/or angioplasty. Diastolic heart sounds were recorded from the $4^{th}$ intercostal space on the chest of patients using a highly sensitive accelerometer, for example a microphone available from Hewlett Packard, Palo Alto, Calif., or a accelerometer transducer, in conjunction with a conventional portable digital pulse code modulation (PCM) data recorder. The output of a finger plethysmograph was also recorded as a timing reference to aid in locating the diastolic period. Next, the data was loaded from the digital tape to a computer, e.g., a HP 9000 from Hewlett Packard, Palo Alto, Calif., using a conventional data acquisition system, e.g., model number 3852A, commercially available from Hewlett Packard. These sounds were recorded while the patients held their breath and were supine.

Before analysis, the data quality was checked. Those records that contain artifacts such as stomach sounds, respiratory noise, unusual background noise, or tape dropouts were eliminated using an automated system. The data were normalized by dividing the overall system gain. For each patient 10 cardiac cycles were digitized with a sampling frequency of 4 kilohertz (kHz). As detailed in J. Semmlow, et al., *Coronary Artery Disease-Correlates Between Diastolic Auditory Characteristic and Coronary Artery Stenoses*, IEEE Trans. Biomed. Eng., 30:136–139, 1983 and M. Akay, et al., *Detection of Coronary Occlusions Using AR Modeling of Diastolic Heart Sounds*, IEEE Trans on Biomed Eng., 37:366–373 (1990), both of which are hereby incorporated by reference in their entirety. The diastolic heart sounds were passed through an anti-aliasing analog filter set for a cutoff frequency of 1200 Hz and a highpass digital filter set for a cutoff frequency of 200 Hz.

Figure 5A:
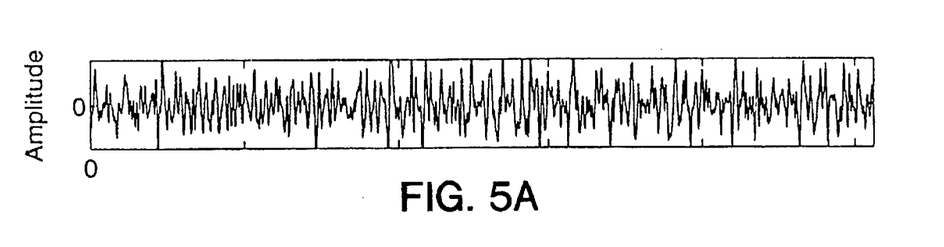
FIG. 5a illustrate the diastolic heart sounds for a diseased patient.
Figure 5B:
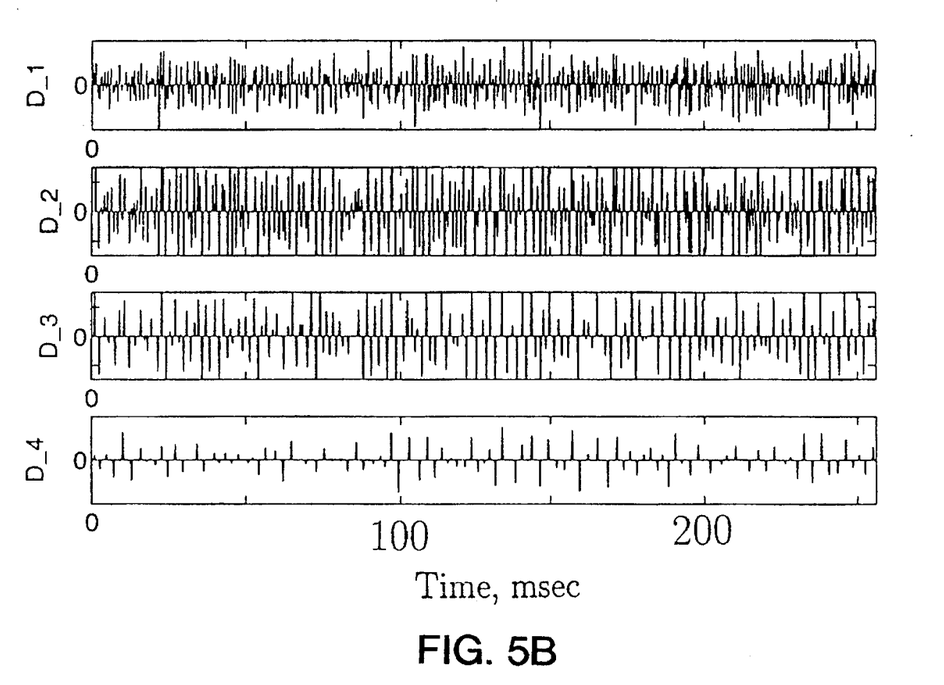
FIG. 5b illustrating the extrema of four wavelet transform bands for a diseased patient.
Figure 6A:
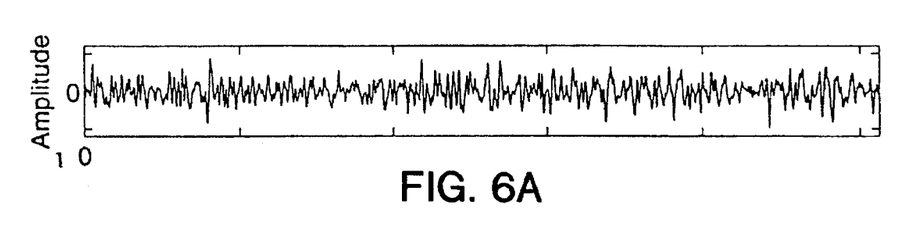
FIG. 6a the diastolic heart sounds for a healthy patient.
Figure 6B:
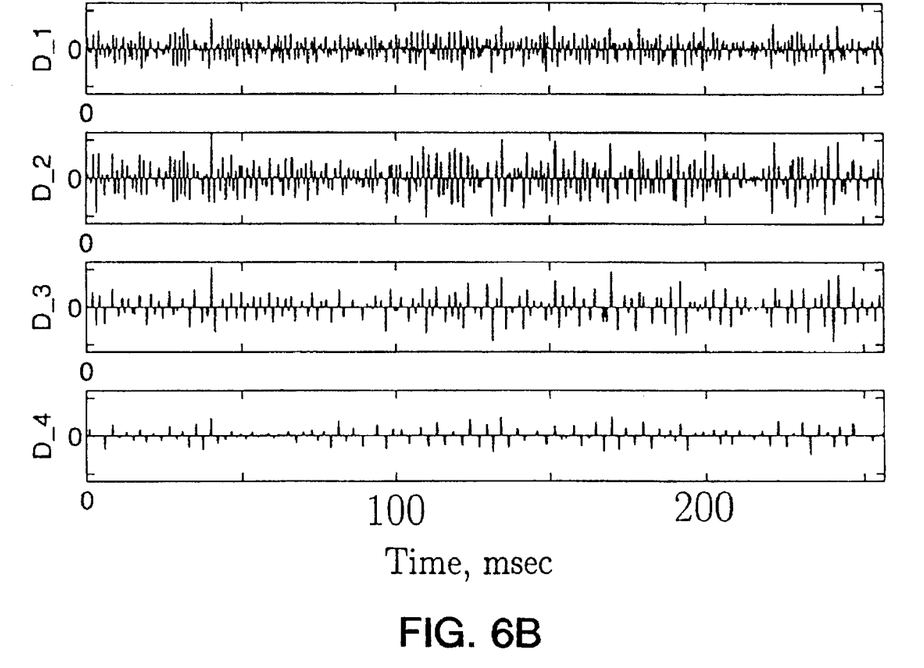
FIG. 6b illustrating the extrema of four wavelet transform bands for a healthy patient.

The extrema of the fast wavelet transform coefficients of diastolic heart sounds were calculated for a period. Then, the first four moments, as defined above, were averaged over 10 cardiac cycles for each patient. For each patient, the feature pattern consists of 10 parameters. Of these parameters, 4 were obtained from the analysis of the diastolic heart sounds associated with CAD, i.e., the first 4 moments of the extrema of the signal at the third scale, labeled "D3" on FIGS. 5B and 6B. The signal at the third scale was chosen since this band was the most discriminative in separating normal subjects from abnormal subjects in previous studies. Thereafter, the first 4 moments were averaged over 10 cardiac cycles for each patient. FIGS. 5a and 5b illustrate the diastolic heart sounds for a typical diseased subject and the corresponding extrema of four wavelet bands. FIGS. 6a and 6b illustrate the diastolic heart sounds for a typical healthy subject and the corresponding extrema of four wavelet bands. For diagnosis purposes only the second and third wavelet bands were used. These four parameters, i.e., the four moments, and the six CEP, described above, were used to generate a 10-point feature vector as the input to the neural networks, for each recording. As discussed above with respect to the CEP, each of the parameters was normalized with respect to the highest value of each parameter in the data base.

The remaining 6 parameters were taken from physical exam records. The physical exam parameters of the feature pattern were sex (s), age (a), systolic blood pressure (sp), diastolic blood pressure (dp), smoking condition (sc), and body weight (bw). These parameters were used because they are significant to the diagnosis of coronary artery disease.

As discussed above, the parameters age (a), diastolic blood pressure (dp), systolic blood pressure (sp), and body weight (bw) were scaled as analog values between 0.0 and 1.0. The remaining physical exam parameters—sex (s) and smoking condition (sc)—were coded in binary manner where 1 represents a male as well as a smoker since the risk factor for a man and a smoker is much higher than that of a woman and a non-smoker.

The feature pattern was utilized as the input to the neural network. A three layer fuzzy min-max network was used. The testing of the network was achieved by using the hyperbox derived in a training test and applying the new patterns to the network to which it had not been exposed. The network was tested on the 112 patients. Of the 112 patient test cases, 30 were selected for use as training cases for the neural networks. Of these, 15 were normal and 15 were abnormal subjects. Another 55 abnormal and 27 normal subjects were used as testing cases for the neural network. All of these patients, except for 5 pseudo-normal subjects, i.e., they were not cath-proven, were either cath-proven normal or abnormal patients.

A winner-take-all decision rule was used in this study. This means that the input pattern vector was set to the class belonging to the output node whose value is the biggest. All training was done in a supervised fashion, which means that the inputs and desired outputs were known during the training process. Results showed that sensitivity and specificity of the neural networks using only moments were 78% and 89% respectively. Therefore, 43 of 55 abnormal and 24 of 27 normal cases were correctly diagnosed. Sensitivity and specificity of the neural networks using only physical examination parameters were 73% and 79%, respectively. Therefore, 40 out of 55 abnormal and 21 out of 27 normal subjects were correctly identified. In addition, sensitivity and specificity of the neural networks using the combination of the physical examination parameters and the moments of the third wavelet bands of diastolic heart sounds were 85% and 89%, respectively. Therefore, 47 out of 55 abnormal and 24 out of 27 normal subjects were correctly identified. A more detailed discussion of the experimental results is given in Y. Akay, *Noninvasive Detection of Coronary Artery Disease Using Wavelet-based Fuzzy Neural Networks*, IEEE Eng. in Med. and Bio. 761–764 (November/December 1994) that is hereby incorporated by reference in its entirety.

In alternate embodiments of the present invention arterial stenosis can be diagnosed in other arteries, e.g., the carotid artery.

While the invention has been particularly shown and described with reference to a preferred embodiment, it will be understood by persons skilled in the relevant art that various change in form and details can be made therein without departing from the spirit and scope of the invention.

What is claimed is:

1. A method for generating a risk indicator representing a probability of a patient having an arterial stenosis, comprising the steps of:

receiving a first signal representing one or more sound event caused by turbulence of blood flowing in an artery;

performing a wavelet transform on said first signal to provide information on both a frequency localization and a temporal localization of said one or more sound events represented by said first signal;

generating a feature vector having a plurality of parameters, said parameters include parameters resulting from the wavelet transform and a clinical examination; and generating the risk indicator by manipulating said feature vector using a neural network.

2. The method of claim 1, further comprising the step of:

improving a signal-to-noise ratio of said first signal before said first signal is received by increasing a rate of blood flow in said artery of the patient.

3. The method of claim 2, wherein said step of improving said signal-to-noise ratio comprises an application of a vasodilator drug.

4. The method of claim 2, wherein said first signal represents the sound of turbulence caused by blood flowing through an artery during a diastole.

5. The method of claim 4, wherein said artery is a coronary artery.

6. The method of claim 2, wherein said artery is a carotid artery.

7. The method of claim 1, wherein said step of generating the risk indicator includes:

receiving said feature vector;

using said feature vector as an input to a neural network; and determining the risk indicator based upon an output of said neural network.

8. The method of claim 7, wherein said neural network is a fuzzy minimum-maximum neural network.

9. A computer-based system for determining a risk indicator representing a probability of a patient having an arterial stenosis, comprising:

a processor;

a storage medium including:

a wavelet transform determinator, coupled to said processor, said wavelet transform determinator having an input coupled to receive a first signal representing acoustic measurements from blood flowing through an artery, and having an output, for performing a wavelet transform upon said first signal to generate a second signal at said wavelet transform determinator output representing acoustic events in said first signal;

a feature vector generator, having an input coupled to said wavelet transform determinator output, for generating a feature vector based upon said wavelet transform determinator output; and a neural network determinator, having an input coupled to said feature vector generator, for receiving said feature vector and processing said feature vector with a neural network.

10. The system of claim 9, wherein said feature vector generator utilizes scaled clinical examination data to generate said feature vector.

11. The system of claim 10, further comprising a clinical data scaler, coupled to said processor, for modifying clinical examination data to generate scaled clinical examination data to be input into said neural network determinator.

12. The system of claim 11, wherein said clinical examination data includes a sex of the patient and a blood pressure of the patient.

13. The system of claim 9, wherein said wavelet transform determinator transforms said first signal to provide both frequency and temporal localization of acoustic events represented by said first signal.

* * * * *